United States Patent [19] [11] 4,402,727
Förster et al. [45] Sep. 6, 1983

[54] SUBSTITUTED AZOLYLALKYL PHENOXYPHENOXYALKANE-CARBOXYLATES AS HERBICIDES AND PLANT GROWTH REGULATORS

[75] Inventors: Heinz Förster, Wuppertal; Ludwig Eue, Leverkusen; Robert Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 377,879

[22] Filed: May 13, 1982

[30] Foreign Application Priority Data

Jun. 4, 1981 [DE] Fed. Rep. of Germany ....... 3122175
Mar. 2, 1982 [DE] Fed. Rep. of Germany ....... 3207484

[51] Int. Cl.$^3$ .................... A01N 43/50; A01N 43/56; C07O 231/12; C07O 233/60
[52] U.S. Cl. .......................... 71/74; 71/92; 548/255; 548/262; 548/341; 548/378
[58] Field of Search .............. 548/255, 262, 341, 378; 71/74, 92

[56] References Cited

PUBLICATIONS

Foerster et al., Chemical Abstracts, vol. 95: (1981), No. 132530u.
Durr et al., Chemical Abstracts, vol. 94: (1981), No. 46981q.

Primary Examiner—Robert W. Ramsuer
Attorney, Agent, or Firm—Sprung, Horn, Kramer & Woods

[57] ABSTRACT

Substituted azolylalkyl phenoxyphenoxyalkanecarboxylates of the formula

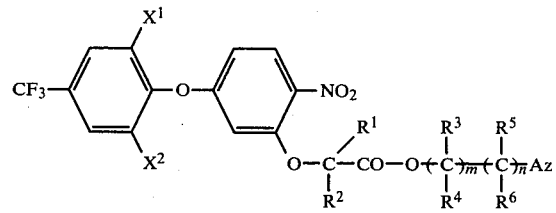

in which
$X^1$ and $X^2$ each independently is a hydrogen or halogen atom,
$R^1$, $R^2$, $R^3$, $R^4$, $R^5$ and $R^6$ each independently is hydrogen or an alkyl group having 1 to 4 carbon atoms,
m is 1 or 2,
n is 0 or 1, and
Az represents an optionally substituted azolyl radical, or an addition pocket thereof with an acid, metal salt or quaternary-forming alkylating agent, which possess herbicidal and plant growth-regulating activity. Intermediates therefor are also new.

13 Claims, No Drawings

SUBSTITUTED AZOLYLALKYL PHENOXYPHENOXYALKANE-CARBOXYLATES AS HERBICIDES AND PLANT GROWTH REGULATORS

The invention relates to certain new substituted azolylalkyl phenoxyphenoxyalkanecarboxylates, to several processes for their production, and to their use as herbicides and plant growth regulators.

It has already been disclosed that certain phenoxyphenoxyalkanecarboxylates possess herbicidal properties (see German Published Specification DOS 2,311,638 and U.S. Pat. No. 4,093,446). Thus, for example, ethyl α-(5-(2-chloro-4-trifluoromethylphenoxy)-2-nitrophenoxy)-propionate can be used for combating weeds. The action of this compound is good, but the selectivity is not always adequate.

The present invention now provides, as new compounds, the substituted azolylalkyl phenoxyphenoxyalkanecarboxylates of the general formula

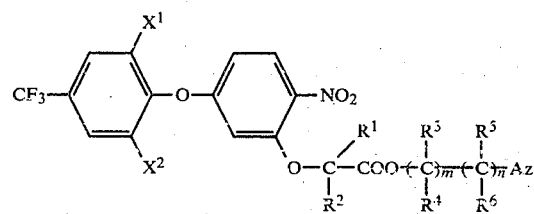

in which
X¹ and X² independently of each other represent a hydrogen or halogen atom,
R¹, R², R³, R⁴, R⁵ and R⁶ independently of one another represent a hydrogen atom or an alkyl group having 1 to 4 carbon atoms,
m represents 1 or 2,
n represents 0 or 1 and
Az represents an optionally substituted azolyl radical,
or their acid addition salts, metal salt complexes or alkylating agent quaternary addition salts.

According to the present invention we further provide a process for the production of a compound of the present invention, characterized in that (a) a phenoxyphenoxyalkanecarboxylic acid-chloride of the general formula

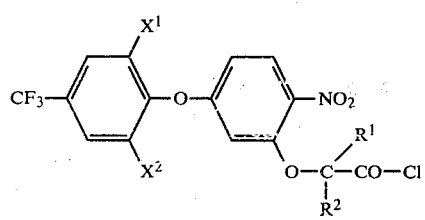

in which
X¹, X², R¹ and R² have the meanings given above,
is reacted with a hydroxyalkylazole of the general formula

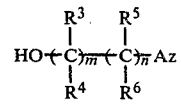

in which
R³, R⁴, R⁵, R⁶, Az, m and n have the meanings given above,
if appropriate in the presence of an acid acceptor and, if appropriate, in the presence of a diluent, or
(b) a phenoxyphenol of the general formula

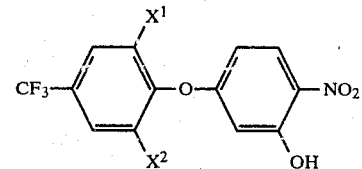

in which
X¹ and X² have the meanings given above,
is reacted with an azolylalkyl halogenoalkanecarboxylate of the general formula

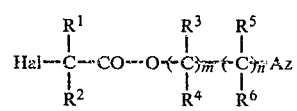

in which
R¹, R², R³, R⁴, R⁵, R⁶, Az, m and n have the meanings given above and
Hal represents a chlorine or bromine atom,
if appropriate in the presence of an acid acceptor and, if appropriate, in the presence of a diluent, or
(c) an azolylalkyl phenoxyphenoxyalkanecarboxylate of the general formula

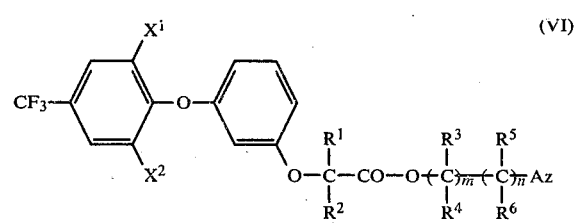

in which
X¹, X², R¹, R², R³, R⁴, R⁵, R⁶, Az, m and n have the meanings given above,
is reacted with nitric acid, if appropriate in the presence of a catalyst and, if appropriate, in the presence of a diluent;
and, if desired, an acid, a metal salt or an alkylating agent is then added onto the azolylalkyl phenoxyphenoxyalkanecarboxylate of the formula (I) obtained by reaction variant (a), (b) or (c).

Finally, it has been found that the novel compounds of the present invention are distinguished by outstanding herbicidal and plant growth-regulating properties.

Surprisingly, the compounds of the present invention possess a substantially better selective herbicidal activity than ethyl α-(5-(2-chloro-4-trifluoromethyl-phenoxy)-2-nitro-phenoxy)-propionate, which is a previously known active compound of similar constitution and identical direction of action. In addition, the compounds according to the invention can also be employed as plant growth regulators. In particular, they can be used as defiolants and desiccants of cotton.

Preferred compounds according to the present invention are those
in which
X$^1$ represents a chlorine atom,
X$^2$ represents a hydrogen or chlorine atom,
R$^1$, R$^2$, R$^3$, R$^4$, R$^5$ and R$^6$ independently of one another represent a hydrogen atom or a methyl group,
m represents 1 or 2,
n represents 0 or 1 and
Az represents an azolyl radical selected from pyrazolyl, imidazolyl, 1,2,4-triazolyl, 1,2,3-triazolyl and 1,3,4-triazolyl, each being bonded via a ring nitrogen atom, the azolyl radical optionally being monosubstituted or polysubstituted by identical or different substituents selected from fluorine, chlorine, bromine, iodine, alkyl having 1 to 4 carbon atoms (which in turn is optionally substituted by fluorine, chlorine, cyano, alkoxy having 1 to 4 carbon atoms, alkylthio having 1 to 4 carbon atoms, alkylsulphinyl having 1 to 4 carbon atoms, alkylsulpho-nyl having 1 to 4 carbon atoms and/or alkoxycarbonyl having 1 to 4 carbon atoms in the alkoxy group), alkoxy having 1 to 4 carbon atoms, alkylthio having 1 to 4 carbon atoms, cyano, carboxyl, alkoxycarbonyl having 1 to 4 carbon atoms in the alkoxy group, alkylcarbonyl having 1 to 4 carbon atoms in the alkyl group and phenyl (which in turn is optionally substituted by halogen, alkyl having 1 to 4 carbon atoms, trifluoromethyl, cyano, nitro and/or alkoxy having 1 to 4 carbon atoms). Particularly preferred compounds according to the invention are those
in which
X$^1$ represents a chlorine atom,
X$^2$ represents a hydrogen or chlorine atom,
R$^1$ represents a methyl group,
R$^2$, R$^3$ and R$^4$ represent a hydrogen atom,
R$^5$ and R$^6$ represent hydrogen or methyl,
m represents 1 or 2,
n represents 0 or 1 and
Az represents an azolyl radical selected from pyrazolyl, imidazolyl, 1,2,4-triazolyl, 1,2,3-triazolyl and 1,3,4-triazolyl, each being bonded via a ring nitrogen atom, the azolyl radical optionally being monosubstituted, disubstituted or trisubstituted by identical or different substituents selected from fluorine, chlorine, bromine, alkyl having 1 or 2 carbon atoms (which in turn is optionally substituted by fluorine, chlorine, cyano, alkoxy having 1 or 2 carbon atoms, alkylthio having 1 or 2 carbon atoms, alkylsulphinyl having 1 or 2 carbon atoms, alkylsulphonyl having 1 or 2 carbon atoms and/or alkoxycarbonyl having 1 or 2 carbon atoms in the alkoxy group), alkoxy having 1 or 2 carbon atoms, alkylthio having 1 or 2 carbon atoms, cyano, carboxyl, alkoxycarbonyl having 1 or 2 carbon atoms in the alkoxy group, alkylcarbonyl having 1 or 2 carbon atoms in the alkyl group and phenyl (which in turn is optionally substituted by fluorine, chlorine, bromine, alkyl having 1 or 2 carbon atoms, trifluoromethyl, cyano, nitro and/or alkoxy having 1 or 2 carbon atoms). Preferred compounds of the present invention, when acid addition salts, in addition to having the radical meanings mentioned as preferred, are particularly preferably those acid addition salts which are formed by the addition of hydrohalic acids (such as hydrobromic acid and, preferably hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid or lactic acid) and sulphonic acids (such as p-toluenesulphonic acid and 1,5-naphthalenedisulphonic acid).

Preferred compounds of the present invention, when metal salt complexes, in addition to having the radical meanings mentioned as preferred, are particularly preferably those metal salt complexes which contain, as cations, metals of the main group II to IV or the subgroups I and II or IV to VIII of the Periodic Table (copper, zinc, manganese, magnesium, tin, iron and nickel being mentioned as examples).

Preferred anions of these metal salt complexes are those which are derived from hydrohalic acids (in particular hydrochloric acid and hydrobromic acid) or from phosphoric acid, nitric acid and sulphuric acids.

Preferred compounds of the present invention, when alkylating agent quaternary addition salts, in addition to having the radical meanings mentioned as preferred, are particularly preferably those quaternary salts which are formed by the addition of alkyl chlorides, bromides and iodides, each having 1 to 4 carbon atoms, or of dialkyl sulphates having 1 to 4 carbon atoms per alkyl group.

If α-(5-(2-chloro-4-trifluoromethylphenoxy)-2-nitrophenoxy)-propionic acid-chloride and 1-hydroxymethylpyrazole are used as starting materials, the course of reaction variant (a) according to the present invention is illustrated by the following equation:

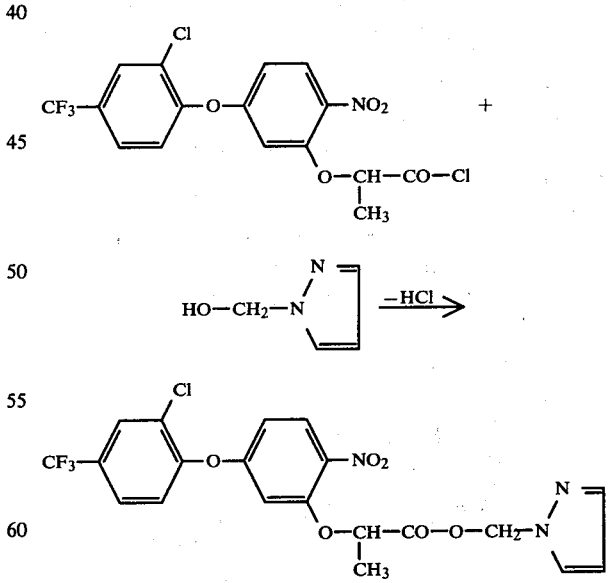

If 5-(2,6-dichloro-4-trifluoromethyl-phenoxy)-2-nitro-phenol and pyrazolyl-methyl α-bromo-propionate are used as starting materials, the course of reaction variant (b) according to the present invention is illustrated by the following equation:

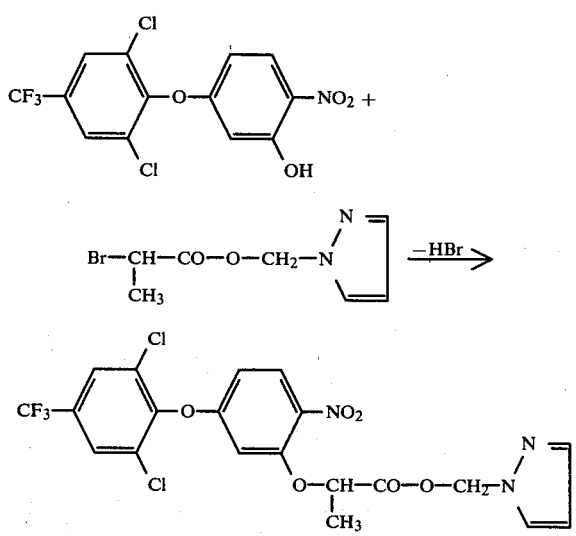

If pyrazolyl-methyl α-(3-(2-chloro-4-trifluoromethyl-phenoxy)-phenoxy)-propionate is used as the starting material and nitric acid is used as the nitrating agent, the course of reaction variant (c) according to the present invention is illustrated by the following equation:

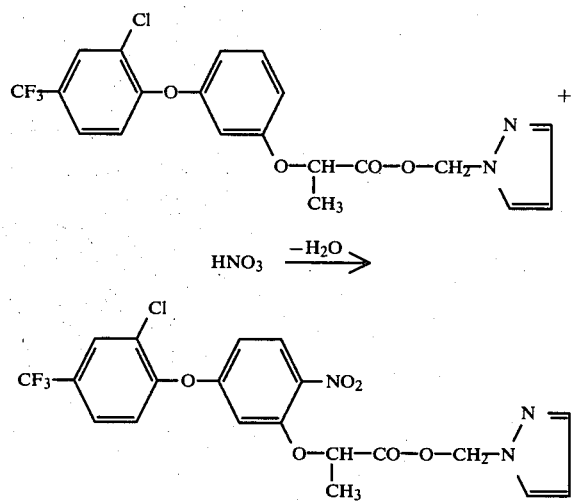

Preferred phenoxyphenoxyalkanecarboxylic acid-chlorides of formula (II) required as starting materials in reaction variant (a) according to the invention are those in which $X^1$, $X^2$, $R^1$ and $R^2$ have those meanings which have already been mentioned in connection with the description of the preferred and particularly preferred compounds according to the present invention.

5-(2-Chloro-4-trifluoromethyl-phenoxy)-2-nitro-phenoxy-acetic acid-chloride, 5-(2,6-dichloro-4-trifluoromethyl-phenoxy)-2-nitro-phenoxy-acetic acid-chloride, α-(5-(2-chloro-4-trifluoromethyl-phenoxy)-2-nitro-phenoxy)propionic acid-chloride and α-(5-(2,6-dichloro-4-trifluoromethyl-phenoxy)-2-nitro-phenoxy)-propionic acid-chloride may be mentioned as examples of compounds of formula (II).

The compounds of the formula (II) are already known (see German Published Specification DOS 2,906,237).

Preferred hydroxyalkylazoles of formula (III) further to be used as starting materials in reaction variant (a), are those in which $R^3$, $R^4$, $R^5$, $R^6$, Az, m and n have those meanings which have already been mentioned in connection with the description of the preferred and particularly preferred compounds according to the present invention.

The following may be individually mentioned as examples of hydroxyalkylazoles of the formula (III): 1-hydroxymethyl-pyrazole, 1-(1-hydroxyethyl)-pyrazole, 1-hydroxymethylimidazole, 1-(1-hydroxyethyl)-imidazole, 1-hydroxymethyl-1,2,4-triazole, 1-(1-hydroxyethyl)-1,2,4-triazole, 1-hydroxymethyl-1,3,4-triazole, 1-(1-hydroxyethyl)-1,3,4-triazole, 1-hydroxymethyl-3,5-dimethylpyrazole, 1-hydroxymethyl-2-methyl-imidazole, 1-hydroxymethyl-3-methyl-pyrazole, 3-chloro-1-hydroxymethyl-1,2,4-triazole, 4-chloro-1-hydroxymethyl-pyrazole, 1-hydroxymethyl-4-methyl-pyrazole, 1-hydroxymethyl-4-methoxy-pyrazole, 1-hydroxymethyl-3-methylthio-pyrazole, 4-chloro-1-hydroxymethyl-3,5-dimethyl-pyrazole, 1-(2-hydroxyethyl)pyrazole, 1-(2-hydroxyethyl)-imidazole and 1-(2-hydroxy-1,1-dimethyl-ethyl)-1,2,4-triazole.

The compounds of the formula (III) are already known (see German Published Specifications DOS 2,835,157 and 2,835,158).

Preferred phenoxyphenols of formula (IV) required as starting materials in reaction variant (b) according to the invention are those in which $X^1$ and $X^2$ have those meanings which have already been mentioned in connection with the description of the preferred and particularly preferred compounds according to the present invention.

5-(2-Chloro-4-trifluoromethyl-phenoxy)-2-nitro-phenol and 5-(2,6-dichloro-4-trifluoromethyl-phenoxy)-2-nitro-phenol may be mentioned as examples.

The compounds of the formula (IV) are already known (see U.S. Pat. No. 3,928,416).

Preferred azolylalkyl halogenoalkanecarboxylates of formula (V) further to be used as starting materials in reaction variant (b) are those in which $R^1$, $R^2$, $R^3$, $R^4$, $R^5$, $R^6$, Az, m and n have those meanings which have already been mentioned in connection with the description of the preferred and particularly preferred compounds according to the present invention, of the formula (I), and Hal represents a chlorine or bromine atom.

The following may be mentioned as examples of the compounds of the formula (V): pyrazol-1-yl-methyl, (1-pyrazol-1-yl)-ethyl, imidazol-1-yl-methyl, 1,2,4-triazol-1-yl-methyl, 1,3,4-triazol-1-yl-methyl, (3,5-dimethylpyrazol-1-yl)-methyl, (2-methyl-imidazol-1-yl)-methyl, (3-methyl-pyrazol-1-yl)-methyl, (3-chloro-1,2,4-triazol-1-yl)-methyl, (4-chloro-pyrazol-1-yl)-methyl, (4-methyl-pyrazol-1-yl)-methyl, (4-methoxypyrazol-1-yl)-methyl, (3-methylthio-pyrazol-1-yl)-methyl and (4-chloro-3,5-dimethylpyrazol-1-yl)-methyl bromoacetate, chloroacetate, α-bromopropionate and α-chloropropionate.

The compounds of the formula (V) have not yet been described in the literature and form a further subject of the present invention. The novel compounds of formula (V) can be prepared in a simple manner by processes which are in themselves known.

The present invention further provides a process for the production of a compound of formula (V), characterised in that a halogenocarboxylic acid-halide of the general formula

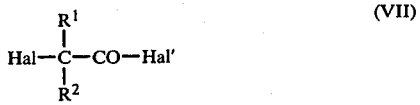
(VII)

in which
R[1] and R[2] have the meanings given above and
Hal and Hal' independently represent a chlorine or bromine atom,
is reacted with a hydroxyalkylazole of the general formula

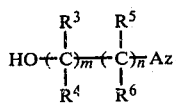
(III)

in which
R[3], R[4], R[5], R[6], Az, m and n have the meanings given above,
if appropriate in the presence of an acid acceptor and, if appropriate, in the presence of a diluent.

Preferred halogenocarboxylic acid-halides of formula (VII) required as starting materials in the above process are those in which R[1] and R[2] have those meanings which have already been mentioned in connection with the description of the preferred and particularly preferred compounds according to the present invention and Hal and Hal' independently represent a chlorine or bromine atom.

Chloroacetyl chloride, bromoacetyl chloride, bromoacetyl bromide, α-chloro-propionic acid-chloride, α-bromopropionic acid-chloride and α-bromopropionic acid-bromide may be mentioned as examples of the compounds of the formula (VII).

The compounds of the formula (VII) are known.

In the above process, the reaction conditions correspond in detail to those of reaction variant (a) according to the invention.

Preferred azolylalkyl phenoxyphenoxyalkanecarboxylates of formula (VI) required as starting materials in reaction variant (c) according to the invention are those in which X[1], X[2], R[1], R[2], R[3], R[4], R[5], R[6], Az, m and n have those meanings which have already been mentioned in connection with the description of the preferred and particularly preferred compounds according to the present invention.

The following may be mentioned as examples of the compounds of the formula (VI): pyrazol-1-yl-methyl, (1-pyrazol-1-yl)-ethyl, imidazol-1-yl-methyl, 1,2,4-triazol-1-yl-methyl, 1,3,4-triazol-1-yl-methyl, (3,5-dimethylpyrazol-1-yl)-methyl, (2-methyl-imidazol-1-yl)-methyl, (3-methyl-pyrazol-1-yl)-methyl, (3-chloro-1,2,4-triazol-1-yl)-methyl, (4-chloro-pyrazol-1-yl)-methyl, (4-methylpyrazol-1-yl)-methyl, (4-methoxy-pyrazol-1-yl)-methyl, (3-methylthio-pyrazol-1-yl)-methyl and (4-chloro-3,5-dimethylpyrazol-1-yl)-methyl 3-(2-chloro-4-trifluoromethylphenoxy)- and 3-(2,6-dichloro-4-trifluoromethyl-phenoxy)phenoxyacetate and -α-phenoxy-propionate.

The compounds of the formula (VI) have not yet been described in the literature and form a further subject of the present invention. The novel compounds of formula (VI) can be prepared in a simple manner by processes which are in themselves known.

The present invention further provides a process for the production of a compound of formula (VI), characterized in that a phenoxyphenol of the general formula

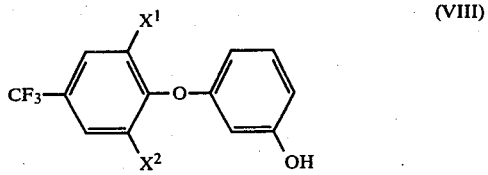
(VIII)

in which
X[1] and X[2] have the meaning given above,
is reacted with an azolylalkyl halogenoalkanecarboxylate of the general formula

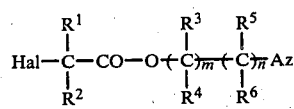
(V)

in which
R[1], R[2], R[3], R[4], R[5], R[6], Az, m, n and Hal have the meanings given above,
if appropriate in the presence of an acid acceptor and, if appropriate, in the presence of a diluent.

Preferred phenoxyphenols of formula (VIII) required as starting materials in the above process are those in which X[1] and X[2] have those meanings which have already been mentioned in connection with the description of the preferred and particularly preferred compounds according to the present invention.

3-(2-Chloro-4-trifluoromethyl-phenoxy)-phenol and 3-(2,6-dichloro-4-trifluoromethyl-phenoxy)-phenol may be mentioned as examples of the compounds of the formula (VIII).

The compounds of the formula (VIII) are already known (see U.S. application Ser. No. 10,288, filed Feb. 8, 1979, now pending.

In the above process, the reaction conditions correspond in detail to those of reaction variant (b) according to the invention.

Reaction variant (a) according to the invention is preferably carried out in the presence of a diluent. Virtually any of the inert organic solvents are suitable diluents of this type. These include, in particular, aliphatic and aromatic, optionally halogenated hydrocarbons (such as pentane, hexane, heptane, cyclohexane, petroleum ether, petrol, ligroin, benzene, toluene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), esters (such as methyl acetate and ethyl acetate), nitriles (such as acetonitrile and propionitrile), amides (such as dimethylformamide, dimethylacetamide and N-methyl-pyrrolidone), dimethylsulphoxide, tetramethylenesulphone and hexamethylphosphoric acid triamide.

Any of the customary acid-binding agents can be used as acid acceptors in reaction variant (a) according to the invention. These preferably include alkali metal carbonates and alcoholates (such as sodium and potassium carbonate, sodium and potassium methylate or ethylate) or aliphatic, aromatic or heterocyclic amines (for example triethylamine, trimethylamine, dimethylaniline, dimethylbenzylamine and pyridine).

In reaction variant (a) according to the invention, the reaction temperatures can be varied within a relatively wide range. In general, the reaction is carried out at a temperature between −20° and +100° C., preferably between 0° and 80° C.

In general, reaction variant (a) according to the invention is carried out under normal pressure.

In carrying out reaction variant (a) according to the invention, in general from 0.9 to 1.5 mols, preferably from 1.0 to 1.3 mols, of hydroxyalkylazole of the formula (III) and, if appropriate, from 1 to 1.5 mols, preferably from 1.05 to 1.3 mols, of acid acceptor are employed per mol of phenoxyphenoxyalkanecarboxylic acid-chloride of the formula (II). Owing to the slightly exothermic course of the reaction, the starting components are preferably combined whilst being cooled with ice and then stirring at a somewhat higher temperature, until the end of the reaction. The working-up is effected according to customary methods. For example, the mixture is diluted with toluene and washed with water, and the organic phase is dried, filtered and concentrated. The residual products in this process are characterized by their melting points.

Reaction variant (b) according to the invention is preferably carried out in the presence of a diluent. Preferred diluents in this process are any of those solvents which have already been mentioned in connection with the description of reaction variant (a) according to the invention as being preferred.

Reaction variant (b) according to the invention is preferably carried out in the presence of an acid acceptor. Preferred acid acceptors in this process are those acid-binding agents which have already been mentioned in connection with the description of reaction variant (a) according to the invention as being preferred.

Even in the case of reaction variant (b) according to the invention, the reaction temperatures can be varied within a relatively wide range. In general, the reaction is carried out at a temperature between 0° and 100° C., preferably between 10° and 80° C.

In general, reaction variant (b) according to the invention is carried out under normal pressure.

In carrying out reaction variant (b) according to the invention, in general from 0.9 to 1.5 mols, preferably from 1.0 to 1.3 mols, of azolylalkyl halogenoalkanecarboxylates of the formula (V) and, if appropriate, from 1 to 1.5 mols, preferably from 1.05 to 1.3 mols, of acid acceptor are employed per mol of phenoxyphenol of the formula (IV).

The starting materials are combined at room temperature and are stirred until the end of the reaction, if appropriate at a slightly elevated temperature. The working-up is carried out according to customary methods, for example as described above.

Reaction variant (c) according to the invention is carried out using a diluent if appropriate. Preferred diluents in this process are halogenated hydrocarbons (such as methylene chloride).

Reaction variant (c) according to the invention is carried out, if appropriate, in the presence of a catalyst. Preferred catalysts are protonic acids (such as sulphuric acid or acetic acid).

In reaction variant (c), the reaction temperature is kept in general between −20° and +80° C., preferably between 0° and 50° C. In general, reaction variant (c) is carried out under normal pressure.

To carry out reaction variant (c) according to the invention, in general from 0.9 to 2 mols, preferably from 1.0 to 1.3 mols, of nitric acid and, if appropriate, about the same quantity of a catalyst are employed per mol of azolylalkyl phenoxyphenoxyalkanecarboxylates of the formula (VI). The starting components are preferably combined while being cooled with ice and are then stirred until the end of the reaction, if appropriate at a slightly elevated temperature.

The working-up is carried out according to customary methods, for example by pouring the mixture into ice water, filtering under suction and recrystallizing if appropriate.

Preferred acids for the preparation of acid addition salts of the compounds of the formula (I) are those which have already been mentioned in connection with the description of the acid addition salts according to the invention as being preferred acids.

The acid addition salts of the compounds of the formula (I) can be obtained in a simple manner according to customary methods of salt formation, for example by dissolving a compound of the formula (I) in a suitable inert solvent and adding the acid (for example hydrochloric acid) and can be isolated in a known manner, for example by filtration, and can be purified, if appropriate, by washing with an inert organic solvent.

Preferred anions and cations for the preparation of metal salt complexes of compounds of the formula (I) are those which have already been mentioned in connection with the description of the metal salt complexes according to the invention as being preferred.

The metal salt complexes of compounds of the formula (I) can be obtained in a simple manner according to customary processes, for example by dissolving the metal salt in alcohol (for example ethanol) and adding the solution to the compound of the formula (I). Metal salt complexes can be isolated in a known manner, for example by filtering off, and can be purified, if appropriate, by recrystallization.

Preferred alkyl chlorides, alkyl bromides, alkyl iodides and alkyl sulphates for the preparation of alkylating agent quaternary addition salts of compounds of the formula (I) are those which have already been mentioned in connection with the description of the preferred alkylating agent quaternary addition salts according to the invention.

The alkylating agent quaternary addition salts of the compounds of the formula (I) can be prepared in a simple manner under the conditions customary for alkylations of this type. Thus, the particular quaternary salts are obtained, for example, by dissolving a compound of the formula (I) in an inert organic solvent (such as acetonitrile) and adding the alkylating agent. The quaternary salts, which are produced in crystalline form, can be isolated according to customary methods. In general, the compounds are isolated by filtering off and are purified, if appropriate, by washing with an inert organic solvent.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the invention are particularly suitable for selectively combating weeds in various crops, such as corn, soy beans, cotton and cereal.

The active compounds according to the invention possess a very good plant growth-regulating activity. They are particularly suitable for inhibiting growth, as well as for defoliating and desiccating the leaves of cotton.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents.

In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds or as plant growth regulators, as mixtures with known herbicides or plant growth regulators, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

When used as herbicides, the active compounds according to the invention can be applied either before or after emergence of the plants. They are preferably applied before emergence of the plants, that is to say by the pre-emergence method. They can also be incorporated into the soil before sowing.

As regards the use of the active compounds according to the invention as plant growth regulators, the rule is that they are applied within a preferred period of time, the exact definition of which depends on the climatic and vegetative circumstances.

The amount of active compound used can vary within a substantial range. It depends essentially on the nature of the desired effect. In general, the amounts used are between 0.01 and 50 kg of active compound per hectare of soil surface, preferably between 0.05 and 10 kg per ha.

The present invention also provides herbicidal or plant growth regulant composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLE

EXAMPLE 1

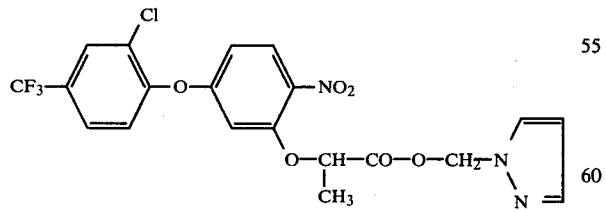

A solution of 21.2 g (0.05 mol) of α-(5-(2-chloro-4-trifluoromethylphenoxy)-2-nitro-phenoxy)-propionic acid-chloride in 30 ml of toluene was added to a mixture, cooled to from 0° to 5° C., of 5.4 g (0.055 mol) of 1-hydroxymethylpyrazole, 6 g (0.06 mol) of triethylamine and 70 ml of toluene. The reaction mixture was stirred overnight (approx. 15 hours) at room temperature (approx. 20° C.). To work up the mixture, it was diluted with toluene and then washed with water, dilute sodium hydroxide solution and again with water, and the organic phase was dried, filtered and concentrated. 17.0 g (70% of theory) of pyrazol-1-yl-methyl α-(5-(2-chloro-4-trifluoromethyl-phenoxy)-2-nitrophenoxy)-propionate were obtained in the form of beige-colored crystals of melting point 75° C.

The compounds listed as formulae in the tables below were prepared according to the method described in Example 1 or also according to reaction variants (b) and (c).

TABLE 1

(Ia)

Structure: CF$_3$-C$_6$H$_2$(Cl)(X$^2$)-O-C$_6$H$_3$(NO$_2$)-O-CH(CH$_3$)-COO-CH$_2$-Az

| Compound No. | X$^2$ | Az | Melting point °C. |
|---|---|---|---|
| 2 | Cl | pyrazol-1-yl | 124 |
| 3 | H | 1,2,4-triazol-1-yl | |
| 4 | Cl | 1,2,4-triazol-1-yl | |
| 5 | H | 3-methylpyrazol-1-yl | |
| 6 | Cl | 3-methylpyrazol-1-yl | |
| 7 | H | imidazol-1-yl | |
| 8 | Cl | imidazol-1-yl | |

TABLE 1-continued

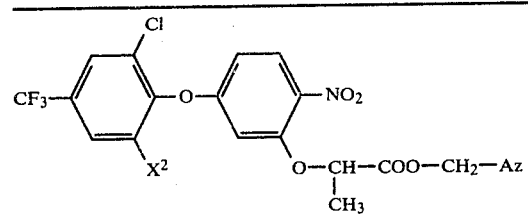

(Ia)

| Compound No. | $X^2$ | Az | Melting point °C. |
|---|---|---|---|
| 9 | H | -N-N=C(CH₃)- (pyrazole with CH₃) | |
| 10 | Cl | -N-N=C(CH₃)- (pyrazole with CH₃) | |
| 11 | H | -N-N=C(Cl)- (triazole with Cl) | |
| 12 | Cl | -N-N=C(Cl)- (triazole with Cl) | |
| 13 | H | pyrazole-CH₃ | |
| 14 | Cl | pyrazole-CH₃ | |
| 15 | H | pyrazole-Cl | |
| 16 | Cl | pyrazole-Cl | |
| 17 | H | pyrazole-Cl | |

TABLE 1-continued

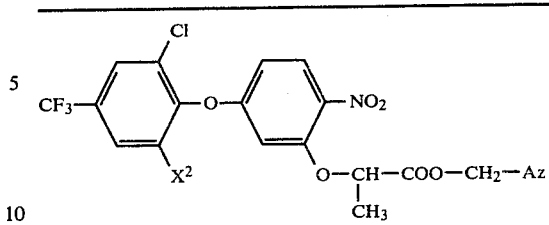

(Ia)

| Compound No. | $X^2$ | Az | Melting point °C. |
|---|---|---|---|
| 18 | Cl | pyrazole-Cl | |
| 19 | H | pyrazole-CH₃ | |
| 20 | Cl | pyrazole-CH₃ | |
| 21 | H | pyrazole-OCH₃ | |
| 22 | Cl | pyrazole-OCH₃ | |
| 23 | H | pyrazole-SCH₃ | |
| 24 | Cl | pyrazole-SCH₃ | |
| 25 | H | pyrazole with H₃C, Cl, CH₃ | |

TABLE 1-continued

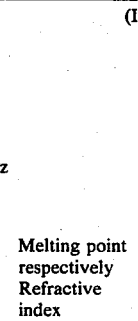

(Ia)

| Compound No. | X² | Az | Melting point °C. |
|---|---|---|---|
| 26 | Cl | 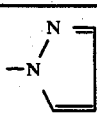 | |

TABLE 2

(I)

[Structure with X¹, X² substituents and Az group]
$$O-\underset{R^2}{\overset{R^1}{C}}-COO(C)_m^{R^3,R^4}(C)_n^{R^5,R^6}Az$$

| Compound No. | X¹ | X² | R¹ | R² | R³ | R⁴ | R⁵ | R⁶ | n | m | Az | Melting point respectively Refractive index |
|---|---|---|---|---|---|---|---|---|---|---|---|---|
| 27 | Cl | Cl | H | CH₃ | H | H | — | — | 0 | 2 | 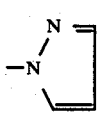 | 116° C. |
| 28 | Cl | H | H | CH₃ | H | H | — | — | 0 | 2 | 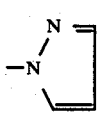 | $n_D^{20} = 1.5528$ |
| 29 | Cl | Cl | H | CH₃ | H | H | — | — | 0 | 2 | 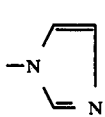 | 98–100° C. |
| 30 | Cl | H | H | CH₃ | H | H | — | — | 0 | 2 | 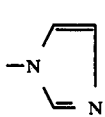 | 174° C. |
| 31 | Cl | Cl | H | CH₃ | H | H | CH₃ | CH₃ | 1 | 1 | 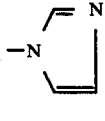 | |
| 32 | Cl | H | H | CH₃ | H | H | CH₃ | CH₃ | 1 | 1 | 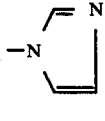 | |

In these examples, the compounds according to the present invention are each identified by the number (given in brackets) from the example and tables hereinabove.

The known comparison compound is identified as follows:

(A) = 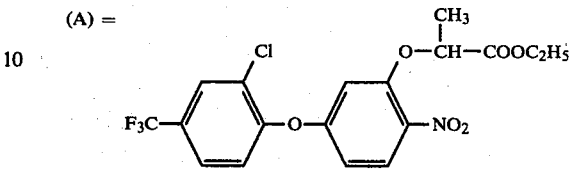

ethyl α-(5-(2-chloro-4-trifluoromethyl-phenoxy)-2-nitrophenoxy)-propionate (disclosed in German Published Specification DOS 2,311,638 or U.S. Pat. No. 4,093,446).

EXAMPLE 2

The herbicidal and plant growth regulant activity of the compounds of this invention is illustrated by the following biotest-examples.

Pre-emergence test
Solvent: 5 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0%=no action (like untreated control)

100%=total destruction

In this test, the active compounds (1) and (2) according to the invention showed a better selective herbicidal activity than the comparative substance (A).

EXAMPLE 3

Defoliation and desiccation of the leaves of cotton

Solvent: 30 parts by weight of dimethylformamide

Emulsifier: 1 part by weight of polyoxyethylene sorbitan monolaurate

To produce a suitable preparation of active compound 1 part by weight of active compound was mixed with the stated amounts of solvent and emulsifier and the mixture was made up to the desired concentration with water.

Cotton plants were grown in a greenhouse until the 5th secondary leaf has unfolded completely. In this stage, the plants were sprayed with the preparations of active compound until dripping wet. After 1 week, the shedding of leaves and the desiccation of the leaves were rated, in comparison with the control plants.

The figures of merit have the following meanings:

0 denoted no desiccation of the leaves, no shedding of leaves

+ denoted slight desiccation of the leaves, slight shedding of leaves

++ denoted severe desiccation of the leaves, severe shedding of leaves.

+++ denoted very severe desiccation of the leaves, very severe shedding of leaves.

In this test, the active compounds (1) and (2) according to the invention showed a very powerful activity.

It will be appreciated that the instant specification and examples are set forth by way of illustration and not limitation, and that various modifications and changes may be made without departing from the spirit and scope of the present invention.

We claim:

1. A substituted azolylalkyl phenoxyphenoxyalkanecarboxylate of the formula

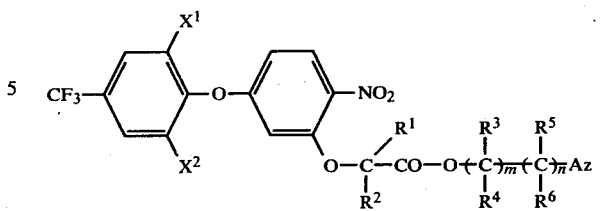

in which $X^1$ and $X^2$ each independently is a hydrogen or halogen atom, $R^1$, $R^2$, $R^3$, $R^4$, $R^5$ and $R^6$ each independently is hydrogen or an alkyl group having 1 to 4 carbon atoms, m is 1 or 2, n is 0 or 1, and Az represents an optionally substituted azolyl radical, or an addition product thereof with an acid, metal salt or quaternary-forming alkylating agent.

2. A compound or addition product according to claim 1, in which $X^1$ represents a chlorine atom, $X^2$ represents a hydrogen or chlorine atom, $R^1$, $R^2$, $R^3$, $R^4$, $R^5$ and $R^6$ independently of one another represent a hydrogen atom or a methyl group, m represents 1 or 2, n represents 0 or 1 and Az represents an azolyl radical selected from pyrazolyl, imidazolyl, 1,2,4-triazolyl, 1,2,3-triazolyl and 1,3,4-triazolyl, each being bonded via a ring nitrogen atom, the azolyl radical optionally being monosubstituted or polysubstituted by identical or different substituents selected from fluorine, chlorine, bromine, iodine, alkyl having 1 to 4 carbon atoms (which in turn is optionally substituted by fluorine, chlorine, cyano, alkoxy having 1 to 4 carbon atoms, alkylthio having 1 to 4 carbon atoms, alkylsulphinyl having 1 to 4 carbon atoms, alkylsulphonyl having 1 to 4 carbon atoms and/or alkoxycarbonyl having 1 to 4 carbon atoms in the alkoxy group), alkoxy having 1 to 4 carbon atoms, alkylthio having 1 to 4 carbon atoms, cyano, carboxyl, alkoxycarbonyl having 1 to 4 carbon atoms in the alkoxy group, alkylcarbonyl having 1 to 4 carbon atoms in the alkyl group and phenyl (which in turn is optionally substituted by halogen, alkyl having 1 to 4 carbon atoms, trifluoromethyl, cyano, nitro and/or alkoxy having 1 to 4 carbon atoms).

3. A compound or addition product according to claim 1, in which $X^1$ represents a chlorine atom, $X^2$ represents a hydrogen or chlorine atom, $R^1$ represents a methyl group, $R^2$, $R^3$ and $R^4$ represent a hydrogen atom, $R^5$ and $R^6$ independently of each other represent hydrogen or methyl, m represents 1 or 2, n represents 0 or 1 and Az represents an azolyl radical selected from pyrazolyl, imidazolyl, 1,2,4-triazolyl, 1,2,3-triazolyl and 1,3,4-triazolyl, each being bonded via a ring nitrogen atom, the azolyl radical optionally being monosubstituted, disubstituted or trisubstituted by identical or different substituents selected from fluorine, chlorine, bromine, alkyl having 1 or 2 carbon atoms (which in turn is optionally substituted by fluorine, chlorine, cyano, alkoxy having 1 or 2 carbon atoms, alkylthio having 1 or 2 carbon atoms, alkylsulphinyl having 1 or 2 carbon atoms, alkylsulphonyl having 1 or 2 carbon atoms and/or alkoxycarbonyl having 1 or 2 carbon atoms in the alkoxy group), alkoxy having 1 or 2 carbon atoms, alkylthio having 1 or 2 carbon atoms, cyano, carboxyl, alkoxycarbonyl having 1 or 2 carbon atoms in the alkoxy group, alkylcarbonyl having 1 or 2 carbon atoms in the alkyl group and phenyl (which in turn is optionally substituted by fluorine, chlorine, bromine, alkyl having 1 or 2 carbon atoms, trifluoromethyl, cyano, nitro and/or alkoxy having 1 or 2 carbon atoms).

4. A compound according to claim 1, wherein such compound is pyrazol-1-yl-methyl α-(5-(2-chloro-4-trifluoromethylphenoxy)-2-nitrophenoxy)-propionate of the formula

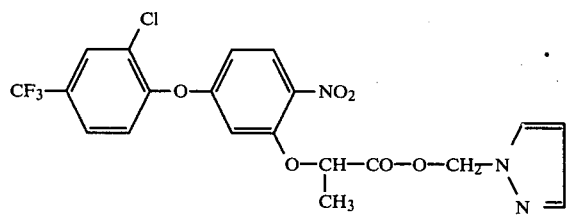

or an addition product thereof with an acid, metal salt or quaternary-forming alkylating agent.

5. A compound according to claim 1, wherein such compound is pyrazol-1-yl-methyl α-(5-(2,6-dichloro-4-trifluoromethylphenoxy)-2-nitrophenoxy)-propionate of the formula

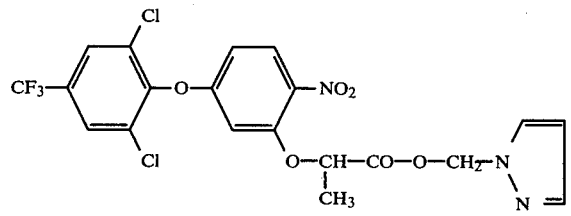

or an addition product thereof with an acid, metal salt or quaternary-forming alkylating agent.

6. A compound according to claim 1, wherein such compound is (2-pyrazol-1-yl)-ethyl α-(5-(2,6-dichloro-4-trifluoromethyl-phenoxy)-2-nitrophenoxy)-propionate of the formula

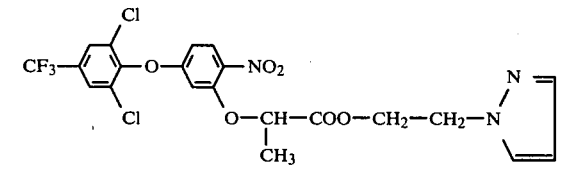

or an addition product thereof with an acid, metal salt or quaternary-forming alkylating agent.

7. A compound according to claim 1, wherein such compound is (2-pyrazol-1-yl)-ethyl α-(5-(2-chloro-4-trifluoromethylphenoxy)-2-nitrophenoxy)-propionate of the formula

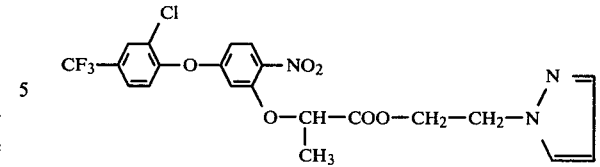

or an addition product thereof with an acid, metal salt or quaternary-forming alkylating agent.

8. A compound according to claim 1, wherein such compound is (2-imidazol-1-yl)-ethyl α-(5-(2,6-dichloro-4-trifluoromethyl-phenoxy)-2-nitrophenoxy)-propionate of the formula

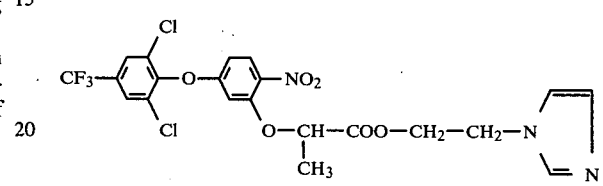

or an addition product thereof with an acid, metal salt or quaternary-forming alkylating agent.

9. A compound according to claim 1, wherein such compound is (2-imidazol-1-yl)-ethyl α-(5-(2-chloro-4-trifluoromethylphenoxy)-2-nitrophenoxy)-propionate of the formula

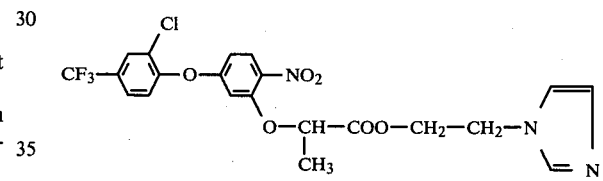

or an addition product thereof with an acid, metal salt or quaternary-forming alkylating agent.

10. A herbicidal defoliating or desicating composition comprising an effective amount of a compound or addition product according to claim 1 in association with a carrier or diluent.

11. A method of combating weeds comprising applying to the weeds, or to a habitat thereof, a herbicidally effective amount of a compound or addition product according to claim 1.

12. A method of defoliating or desiccating plants comprising applying to the plants, or to a habitat thereof, an effective amount of a compound or addition product according to claim 1.

13. The method according to claim 11 or 12, wherein such compound is pyrazol-1-yl-methyl α-(5-(2-chloro-4-trifluoromethylphenoxy)-2-nitrophenoxy)-propionate, pyrazol-1-yl-methyl α-(5-(2,6-dichloro-4-trifluoromethyl-phenoxy)-2-nitrophenoxy)-propionate, (2-pyrazol-1-yl)-ethyl α-(5-(2,6-dichloro-4-trifluoromethyl-phenoxy)-2-nitrophenoxy)-propionate, (2-pyrazol-1-yl)-ethyl α-(5-(2-chloro-4-trifluoromethyl-phenoxy)-2-nitrophenoxy)-propionate, (2-imidazol-1-yl)-ethyl α-(5-(2,6-dichloro-4-trifluoromethyl-phenoxy)-2-nitrophenoxy)-propionate, or (2-imidazol-1-yl)-ethyl α-(5-(2-chloro-4-trifluoromethyl-phenoxy)-2-nitrophenoxy)-propionate, or an addition product thereof with an acid, metal salt or quaternary-forming alkylating agent.

* * * * *